United States Patent
Anderson

[19]

[11] Patent Number: 5,967,154
[45] Date of Patent: Oct. 19, 1999

[54] DENTAL HYGIENE FILAMENT

[75] Inventor: Michael R. Anderson, Boca Raton, Fla.

[73] Assignee: Vision International Production, Inc., Boca Raton, Fla.

[21] Appl. No.: 09/071,911

[22] Filed: May 4, 1998

[51] Int. Cl.[6] .................................................. A61C 15/00
[52] U.S. Cl. .......................... 132/321; 132/323; 132/324
[58] Field of Search .................................... 132/321, 323, 132/324, 329

*Primary Examiner*—John J. Wilson
*Assistant Examiner*—Robyn Doan
*Attorney, Agent, or Firm*—Malin, Haley, DiMaggio & Crosby, PA

[57] ABSTRACT

Dental hygiene filament, for use as dental floss or as bristles for a tooth brush for flossing and/or brushing teeth, comprising an elongated body defining an exterior surface having an abrasive, granular substance, such as pumice, uniformly distributed thereon. The granular material is firmly attached to the filament so that, when used as dental floss, pulling on the ends of the floss between the teeth allows for aggressive and efficient removal of plaque while moving the dental floss across the surface, as recommended by dentists. In addition, the irregular surface area acts to cause additional frictional interaction between the filament's granular material and the tooth surface, quickly and efficiently removing the plaque and providing a greater surface area for removing plaque. Each filament embodiment may include a microbicide for preventing bacterial growth.

3 Claims, 4 Drawing Sheets

DENTAL HYGIENE FILAMENT

BACKGROUND OF THE INVENTION

1. Field of the Invention

This invention relates to dental hygiene filament, and, more particularly to a filament used for dental floss and tooth brush bristles which has an improved ability for removing plaque from teeth by virtue of providing an interdental cleaning filament with an irregular surface profile for improved cleaning efficiency.

2. Description of the Background Art

The primary aim of dental self-care is the prevention of tooth decay and removal of plaque. Plaque is a gummy film made up of polysaccharides and bacteria that adheres to your teeth, particularly along the gum line. Preventing the buildup of plaque is recognized as one of the best ways to avoid tooth decay and periodontal disease. Plaque not only leads to cavities, but also eventually combines with certain minerals in saliva to form tartar (also called calculus). Such deposits, both above and below the gum line, lead to periodontal disease such as gingivitis. Symptoms of periodontal disease include bleeding, swollen and receding gums, bad breath, and, ultimately, loose teeth. In addition, destruction of underlying bone and loss of teeth occur in advanced stages. Accordingly, a number of devices are known in the art for use in dental self-care to prevent the buildup of plaque and food particles from the teeth and gums.

The primary instruments for removing plaque and preventing tooth decay and gum disease rely on filament devices such as the tooth brush and dental floss. Tooth brushes are well known instruments used in dental self-care. The typical tooth brush includes a handle portion and a head portion containing a plurality of bristles. Tooth brush bristles are typically formed of flexible, water-repellent nylon bristles with rounded or tapered ends. The tooth brush, and, specifically, the brush bristles, are maneuvered by the user around the teeth and gums while brushing. Typically, toothpaste, or even baking soda, is used as an abrasive for cleaning surfaces of the teeth. In addition, interdental brushes, which have a cylindrical or conical array of bristles, are commonly used in cleaning spaces between teeth.

Furthermore, flossing is an important part of any dental hygiene program. The benefits of using dental floss or tape for preventing the build-up of plaque and for removing food particles and bacteria from between teeth and below the gum line is well recognized in the dental art. Dental floss and tape (hereinafter "floss") are made of round or flat nylon fiber. Dental floss is typically inserted between teeth at various angles and moved in an up-and-down or back-and-forth motion across the surfaces of the teeth. The string diameter is quite small to allow it to fit between the teeth of people who have very close fitting teeth. One of the great advantages that dental floss has in removing plaque is that plaque readily sticks to the surface of a tooth, requiring some type of mechanical application to remove it. Brushing does not readily access between the teeth sufficiently to remove plaque along the tooth surface, especially near the gum line. If the plaque is not efficiently removed, gingivitis and loss of gum bone can literally cause a person to lose their teeth.

Use of the term dental filament herein shall broadly refer to dental floss, dental tape, and/or tooth brush bristles. One of the problems with using conventional dental hygiene instruments is that it can be very time consuming as the dental filament must be aggressively tensioned against each tooth for adequate plaque removal. Accordingly, there exists a need for an improved dental filament for use with dental hygiene devices, such as dental floss or tape and tooth brushes, for providing improved removal of plaque, food particles and the like.

The present invention provides a more efficient dental filament by improving the mechanical interaction between the filament and the tooth surfaces, thereby requiring less effort by the user and faster removal of plaque residing on the tooth surface, so that one can quickly and readily clean one's teeth by flossing and brushing, greatly reducing the time that it takes for each cleaning.

SUMMARY OF THE INVENTION

Dental filament for use as dental floss, or for use as tooth brush bristles, or the like, for flossing and/or brushing teeth. The dental filament comprises an elongated body having a cross sectional diameter suitable for fitting between teeth, and preferably formed of a plastic or nylon material having a high tensile strength. The exterior surface area of the filament defines an irregular surface and may have attached thereto an abrasive polishing material or granular substance, such as pumice. The granular substance may be integrally incorporated into a resin mix prior to formation of filament strands, or may uniformly distributed over preformed filament strands and attached by a thin adhesive coating. The granular material is firmly attached to the filament so that, when used as dental floss, pulling on the ends of the floss between the teeth allows for aggressive and efficient removal of plaque while moving the dental floss across the surface, as recommended by dentists. In addition, the irregular surface area acts to cause additional frictional interaction between the filament's granular material and the tooth surface, quickly and efficiently removing the plaque and providing a greater surface area for removing plaque. The abrasive polishing material can be any suitable material that does not excessively abrade tooth enamel.

In the dental floss embodiment, the filament can be wound on a spool and placed in a conventional housing to allow for the dental floss to be cut in desired lengths for daily use. Once the floss has been used, it can be conveniently disposed of. In the tooth brush or interdental brush embodiment, the filament is formed into tooth brush bristles.

In an alternate embodiment, the granular material is eliminated and an irregular surface is formed by the filament. For example, the filament may be formed with a notched surface. The filament notches may be any suitable shape, such as U-shaped, V-shaped, circular, or irregularly shaped.

It is further contemplated that dental filament according to the present invention may be preserved against fungal and bacterial contamination by the addition of trichlorophenoxy phenol ("TCPP") an antimicrobial agent known for preventing fungal and bacterial growth and contamination. Such an embodiment is considered particularly desirable since dental hygiene instruments, such as tooth brushes, are exposed to conditions favorable to bacterial growth.

It is an object of this invention to provide a dental filament having an improved, more abrasive or frictional interaction surface for more quickly and easily removing dental plaque from the surface of a tooth.

It is another object of this invention to provide an improved dental floss that allows the user to more quickly complete the task of flossing, while at the same time improving the efficiency and overall removal of the plaque.

It is a further object of this invention to provide improved bristles for tooth brushes and interdental brushes that allows the user to more efficiently clean teeth.

In accordance with these and other objects which will become apparent hereinafter, the instant invention will now be described with particular reference to the accompanying drawings.

DESCRIPTION OF THE PREFERRED EMBODIMENTS

Figure 1:
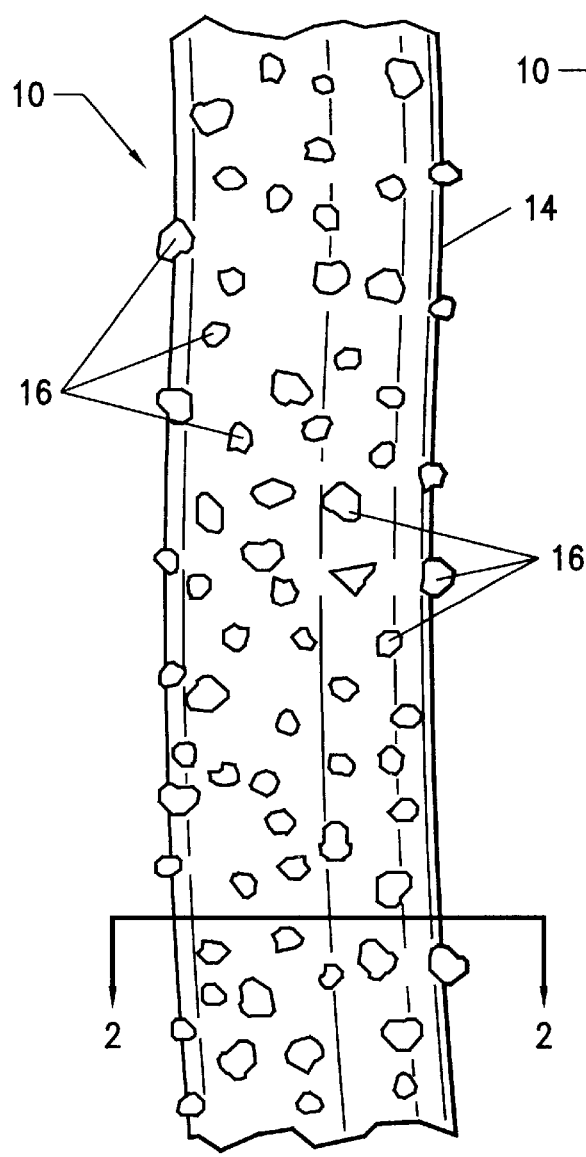
FIG. 1 shows a perspective view of dental filament according to the present invention.
Figure 3:
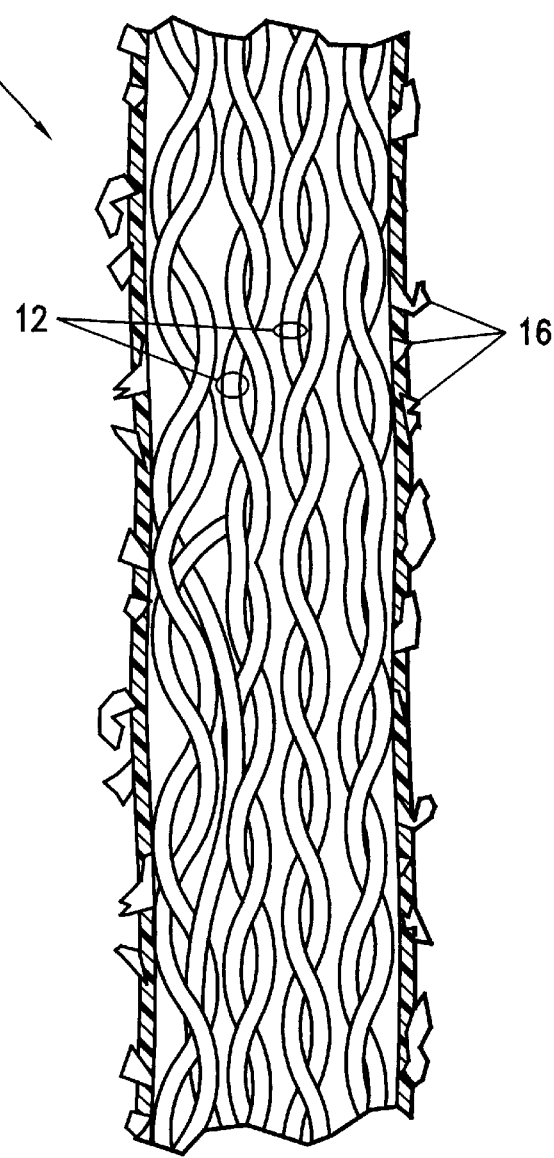
FIG. 3 shows a side sectional view taken along line 3—3 of FIG. 2.
Figure 2:
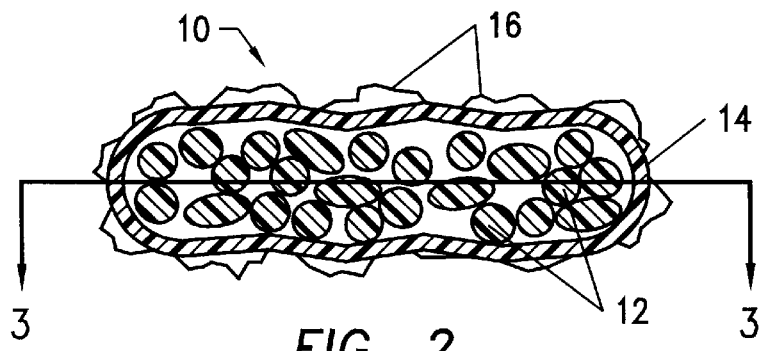
FIG. 2 shows a top plan cross sectional view taken along line 2—2 of FIG. 1.

Referring now to the drawings, FIGS. 1–3 depict a preferred embodiment of dental filament according to the present invention, referenced generally as 10, comprised of a thin, string-like, semi-cylindrical body of a material having high tensile strength. FIG. 1 depicts a length of filament 10 that has been cut at each end, however, it should be readily apparent that filament 10 can be of indefinite length, or can be of a finite length. As best depicted in FIG. 2, filament 10 comprises a plurality of twistedly joined string-like strands 12 having an external coating 14, such as wax. Coating 14 includes a plurality of small granules 16 uniformly distributed thereon and creating an irregular outer surface.

In the preferred embodiment, strands 12 are nylon strands. Nylon is a fiber-forming substance of a long-chain synthetic polyamide. A polyamide is a compound characterized by more than one amide group; an amide is a chemical related to ammonia. In an alternate embodiment, a strands 12 may be fabricated from polytetrafluoroethylene ("PTFE"), which is commercially available under the trademark TEFLON®. In addition, it has been found that silk strands may provide a suitable material for forming dental filament according to the present invention.

In an embodiment wherein filament 10 is used as dental floss, a plurality of individual strands 12, preferably formed from nylon, are twistedly joined into a unitary filament. For example, as best seen in FIG. 2, a plurality of nylon strands 12 are twistedly joined, typically between 2.5 to 3.5 turns per inch, to form a unitary filament for providing increased strength and resistance to fraying or breaking. Unlike dental floss made from nylon, dental floss made from PTFE, however, is preferably formed form a single strand or monofilament. In either case, the dental floss may be coated by dipping in an emulsion bath having any of a variety of coatings such as wax, baking soda, and/or flavoring agents. Coating 14 preferably includes adhesive characteristics for reasons more fully discussed hereinbelow.

FIGS. 1–3 depict a dental filament according to the present invention, generally referenced as 10, formed of a plurality of twistedly joined strands 12. As discussed hereinabove, strands 12 are preferably formed of nylon. Coating 14 is preferably wax, and includes granules 16 uniformly distributed thereon and adhesively secured thereto. Granules 16 may be added to coating material 14 prior to application to strands 12, for example, when the coating material is in a liquid state. Thus, the process of coating the dental filament may also result in the application of granules 16 without the need for additional manufacturing steps. Granules 16 preferably comprise pumice, silica or any suitable abrasive material that is non-toxic and harmless to humans and animals. Granules 16 have an average particle size between about 0.1 and 30 mircons, and preferably between 2 and 15 microns. In addition, granules 16 may comprise dry peroxides or other whitening agents, or any suitable agent for enhancing the appearance of teeth and/or facilitating the removal of plaque, bacteria, food particles and other debris. In an embodiment where strands 12 are formed of PTFE, granules 16 may be added to PTFE in its melted state and prior to formation of individual strands.

Granules 16 are distributed in such a manner and density as to optimize the removal of plaque and debris from the surfaces of teeth. The granules may be of varying sizes, but the sizes are also related to the diameter of the dental filament. Accordingly, the filament outer diameter is preferably sufficiently small to allow for the addition of granules 16 while remaining of a sufficient outer diameter including the granules, which, although not necessarily uniform, is suitably sized to fit interdental spaces.

Figure 4:
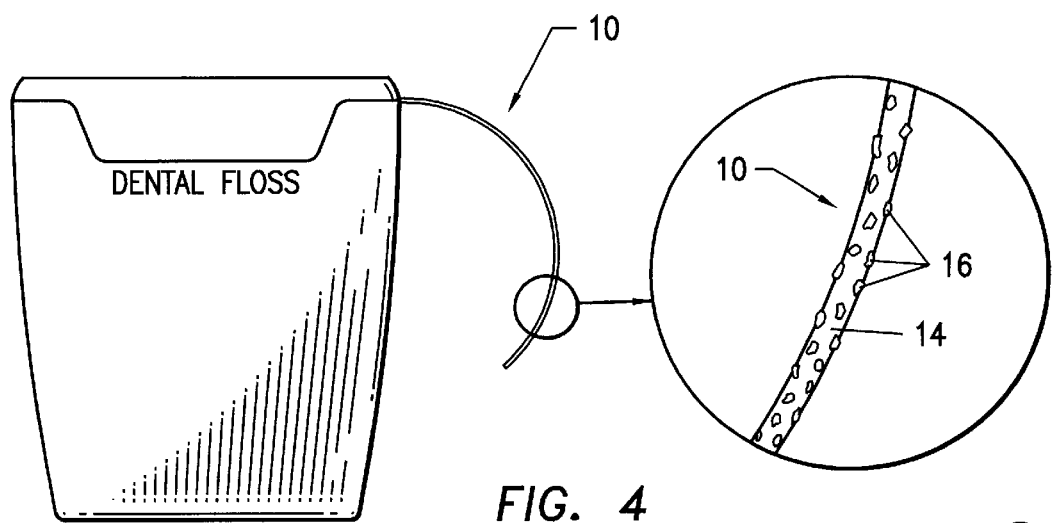
FIG. 4 shows dental filament according to the present invention embodied in dental floss.

FIG. 4 shows filament according to the present invention embodied in dental floss, however, it should be readily apparent that an embodiment in the form of dental tape is considered an equivalent embodiment to the one depicted. The dental floss shown in FIG. 4 is formed of an elongated filament 10 having an outer surface coating 14 which includes granular material 16, such as pumice or silica. To use the present invention, as depicted in FIG. 4, a desired length is cut and the user would wrap the ends of the floss around preferably index fingers. The floss is then applied between the teeth and moved appropriately in an up-anddown and/or side-to-side motion to remove plaque and other debris from the surface of the teeth.

Figure 5:
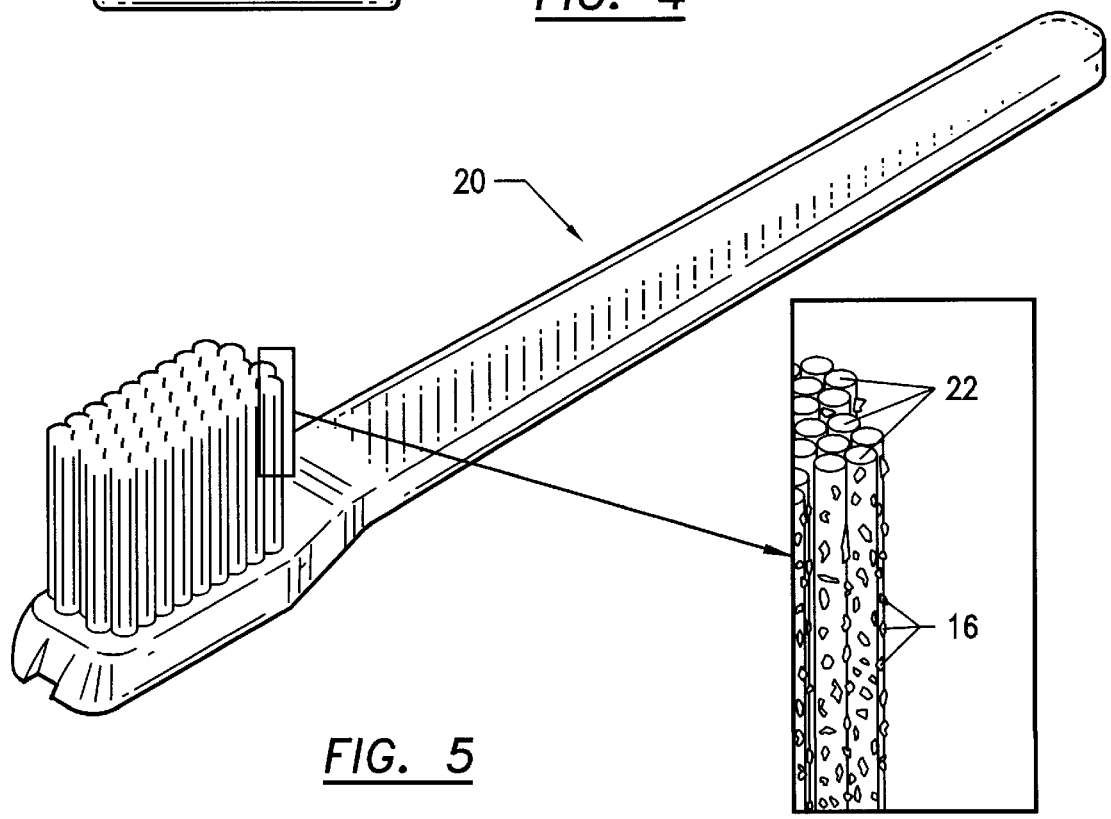
FIG. 5 shows dental filament according to the present invention embodied in tooth brush bristles.

FIG. 5 depicts a tooth brush, generally referenced as 20, having a plurality of monofilament bristles 22 according to an alternate embodiment of the present invention. Each monofilament bristle 22 comprises a mono-filament embodiment of he present invention preferably formed of PTFE, and also includes granular material 16 uniformly distributed on the outer surface thereof. Granular material 16 may be affixed to the outer surface by an adhesive (not shown), or may be added to the PTFE mixture prior to formation such that the granular material 16 is integrally incorporated into thin filament. It should further be apparent that dental filament according to the present invention may be used in connection with any dental brush, such as interdental brushes. The tooth brush depicted in FIG. 5 is used in a conventional manner, however, the irregular bristle surfaces provide an improved capability for removing plaque and other debris.

Figure 6A:
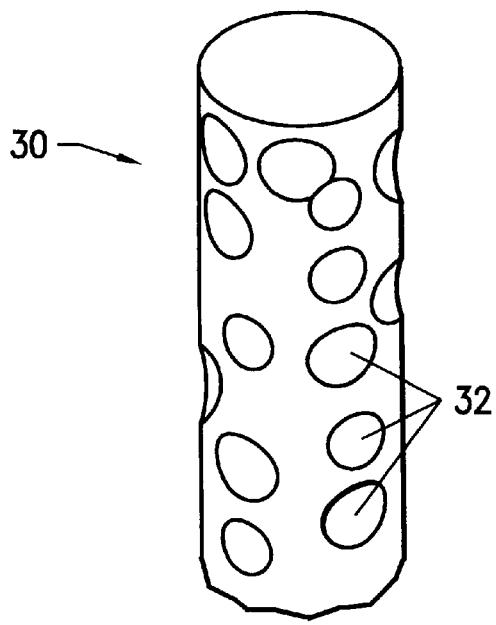
FIG. 6A shows an alternate embodiment of dental filament wherein an irregular outer surface is formed by hemispherical notching.
Figure 6B:
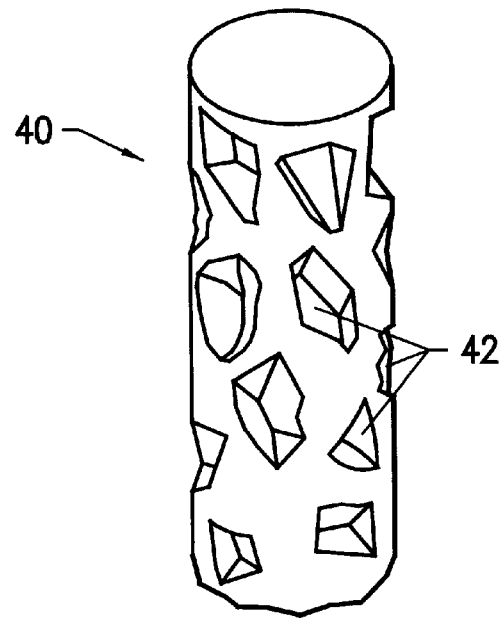
FIG. 6B shows an alternate embodiment of dental filament wherein an irregular outer surface is formed by irregular notching.
Figure 6C:
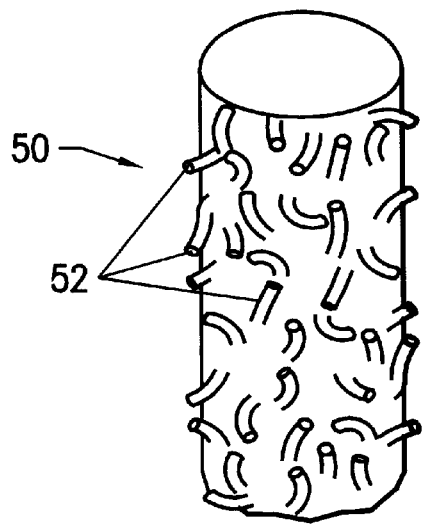
FIG. 6C shows an alternate embodiment of dental filament wherein an irregular outer surface is formed by fiber-like tentacles.
Figure 6D:
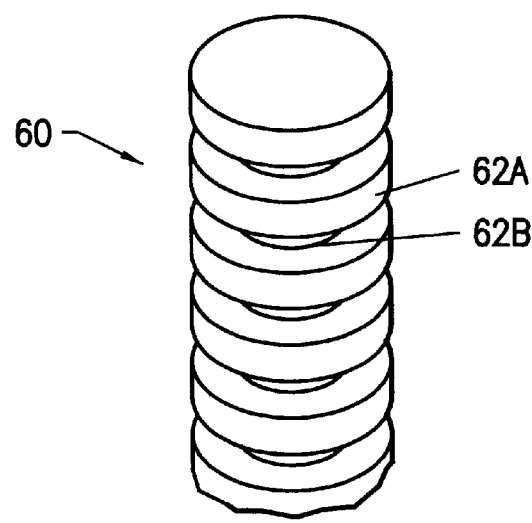
FIG. 6D shows an alternate embodiment of dental filament having irregular cylindrical surfaces.

FIGS. 6A, 6B, 6C, and 6D each show alternate monofilament embodiments for dental filament according to the present invention, such as embodiments formed from single strand PTFE, each having an irregular surface. FIG. 6A shows a first alternate embodiment, referenced as 30, wherein the filament defines an irregular surface formed by semi-spherical depressions 32. FIG. 6B shows a second alternate embodiment, referenced as 40, wherein the filament defines an irregular surface formed by irregular depressions 42. FIG. 6C shows a third alternate embodiment, referenced as 50, wherein the outer surface includes fiber-like tentacles 52. FIG. 6D shows a fourth alternate embodiment, referenced as 60, wherein an irregular surface is formed by alternating disk-like sections of differing radial sizes, referenced as 62A and 62B. In yet another alternate embodiment (not shown), the filament could be molded to provide an irregular surface pattern of increased surface area that would simulate or mimic the granular pumice material in such a fashion as to enhance the interaction between the surface of the tooth and the string body. It should be noted, however, that the use of a granular material, particularly pumice, has been found to provide higher frictional characteristics, which is believed to remove the plaque more efficiently than just plastic contact with the teeth. Furthermore, the present invention is adaptable to a wide variety of dental hygiene instruments. For example, granular material may be added to rubber tips used by dental hygienists to polish teeth such that common toothpaste may be used in lieu of the abrasive polishing compound commonly used.

Figure 7:
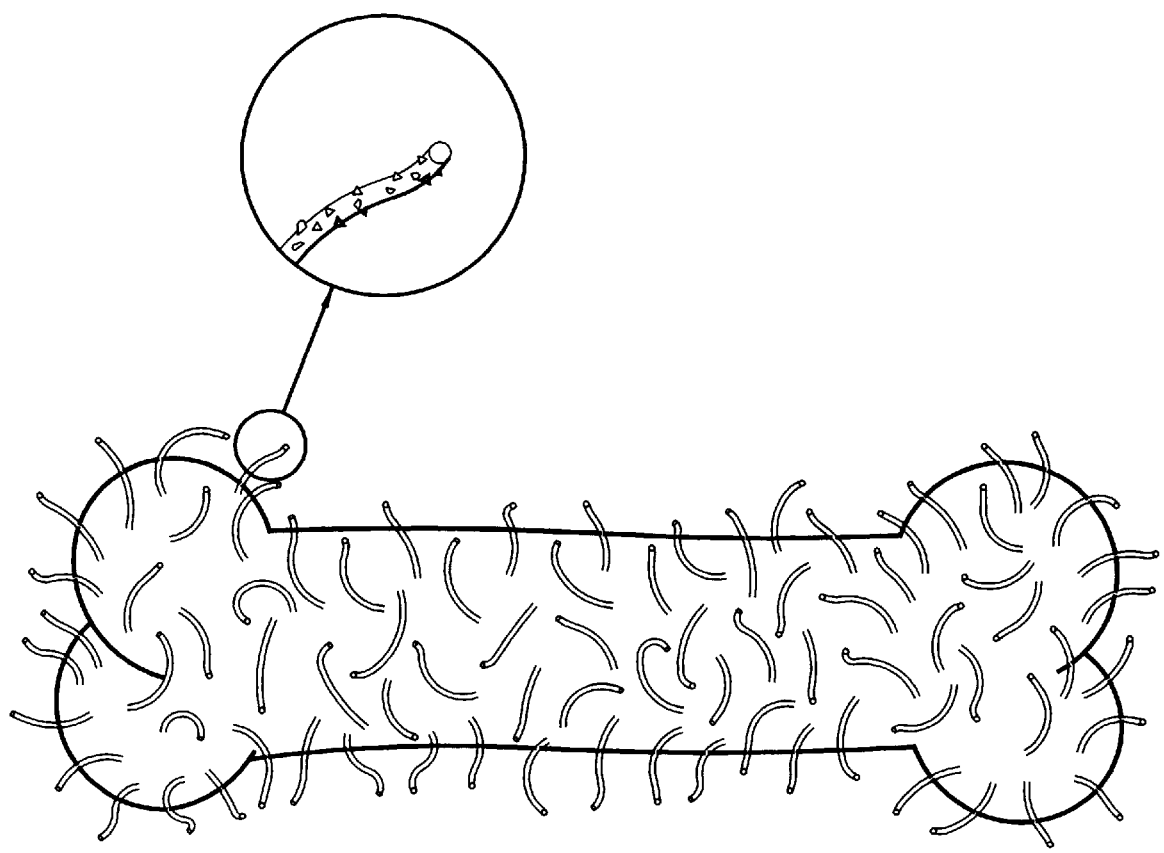
FIG. 7 shows dental filament according to the present invention embodied as bristles on a dog bone.

FIG. 7 shows dental filament according to the present invention embodied as bristles projecting from a dog bone. The embodiment depicted in FIG. 7, is useful in removing plaque and food particles from between the teeth of domestic pets, such as dogs.

Each of the filament embodiments disclosed herein and contemplated by the invention may further include a concentrate of trichlorophenoxy phenol ("TCPP"), such as is available from Morton Plastics Additives, of Danvers, Massachusetts as a product identified as SB-30 comprising a concentrate of trichlorophenoxy phenol in a polymeric resin carrier, which product is sold under the trademark Triclosan®. The chemical TCPP is suitable for use in forming solid polymeric compositions containing a concentration of microbicide. Such resin compositions are protected against fungal or bacterial growth by the incorporation of microbicide therein. It is believed that use of between concentrations of between 1% and 2% by weight Triclosan® based on the total weight of the resin compound is effective in preserving the resin compound against bacterial formations, however, it is contemplated that slightly higher concentrations may be required depending upon the degree of exposure to conditions favorable for bacterial growth.

Accordingly, dental hygiene filament may be formed by adding Triclosan® compound directly to PTFE resin prior to formation of filament strands. In addition, Triclosan® may be used in coatings applied to multi-strand dental floss embodiments. Further still, it is considered desirable to include Triclosan® in resin used to form tooth brush body and handle portions, in addition to the bristles, thereby resulting in a tooth brush having bristles and a body/handle which resist bacterial growth. A further advantage of dental filament embodiments incorporating a microbicide is the ability of the filament to destroy bacteria in the mouth, while present in non-toxic concentrations.

The instant invention has been shown and described herein in what is considered to be the most practical and preferred embodiment. It is recognized, however, that departures may be made therefrom within the scope of the invention and that obvious modifications will occur to a person skilled in the art.

I claim:

1. Dental hygiene filament for use as a dental cleaning implement in removing plaque and food particles from teeth, said filament comDrising:

a plurality of strands twistedly joined to form an elongated flexible filament body said filament body having a coating forming an outer surface, said coating including granular material having the abrasive properties of pumice attached thereto, said granular material and said coating outer surface forming an abrasive irregular filament body outer surface;

wherein said strands each include a microbicide;

wherein said microbicide comprises trichlorophenoxy phenol.

2. Dental hygiene filament for use as a dental cleaning implement in removing plaque and food particles from teeth, said filament comprising:

a plurality of strands twistedly joined to form an elongated flexible filament body;

said filament body having a coating forming an outer surface;

said coating including granular material having the abrasive properties of pumice attached thereto, said granular material and said coating outer surface forming an abrasive irregular filament body outer surface wherein said strand includes a microbicide;

wherein said microbicide comprises trichlorophenoxy phenol.

3. Dental hygiene filament for use as a dental cleaning implement in removing plaque and food particles from teeth, said filament comprising:

a monofilament strand forming an elongated flexible filament body;

said filament body having an outer surface;

said outer surface including granular material having the abrasive qualities of pumice uniformly distributed thereon and attached thereto, said granular material forming an abrasive, irregular outer surface;

wherein said monofilament strand includes a microbicide;

wherein said microbicide comprises trichlorophenoxy phenol.

* * * * *